United States Patent [19]

Matsuyama et al.

[11] Patent Number: 5,672,504
[45] Date of Patent: Sep. 30, 1997

[54] PROCESS FOR ENRICHING AN [R,S]-1,2-EPOXIDE IN ONE ENANTIOMER BY USING MICROBES TO CONVERT ONE ENANTIOMER TO THE OTHER OR TO PREFERENTIALLY OPEN THE EPOXIDE RING

[75] Inventors: Akinobu Matsuyama, Arai; Yoshinori Kobayashi, Joetsu, both of Japan

[73] Assignee: Daicel Chemical Industries, Ltd., Osaka, Japan

[21] Appl. No.: 547,902

[22] Filed: Oct. 25, 1995

Related U.S. Application Data

[63] Continuation of Ser. No. 195,080, Feb. 14, 1994, abandoned.

[30] Foreign Application Priority Data

Feb. 15, 1993 [JP] Japan .................................. 5-025315
Mar. 16, 1993 [JP] Japan .................................. 5-055735

[51] Int. Cl.$^6$ ...................................... C12P 41/00
[52] U.S. Cl. .................. 435/280; 435/123; 435/823; 435/832; 435/834; 435/839; 435/849; 435/875; 435/877; 435/881; 435/920; 435/917; 435/918
[58] Field of Search ................................ 435/280, 123, 435/823, 832, 834, 839, 849, 875, 877, 917, 918, 920

[56] References Cited

U.S. PATENT DOCUMENTS

| | | | |
|---|---|---|---|
| 4,732,853 | 3/1988 | Whitesides | 435/280 |
| 4,923,810 | 5/1990 | Walts | 435/280 |
| 5,273,895 | 12/1993 | Rossi et al. | 435/280 |
| 5,278,070 | 1/1994 | Shum | 435/280 |

FOREIGN PATENT DOCUMENTS

| | | |
|---|---|---|
| 3-133034 | 2/1985 | European Pat. Off. . |
| 1-386848 | 9/1990 | European Pat. Off. . |
| 1-496001 | 7/1992 | European Pat. Off. . |
| 62-296888 | 12/1987 | Japan . |
| 8-700468 | 2/1987 | Netherlands . |

OTHER PUBLICATIONS

Weijers et al., Enzyme Microb. Technol 10:214–218 (1988).
Weijers et al., Enzyme Microb. Technol 13:306–308 (1991).
ATCC Catalogue of Bacteria pp. 270,279 (1992).
Weijers et al., Appl. Microbiol Biotechnol 27:337–340 (1988).
Chen et al. (1994) J. Org. Chem , 58 , 5528–32.
Chemical Abstracts, vol. 109, No. 1, Abstract No. 5300b (1988).
Biological Abstracts, vol. BA94, Abstract No. 3938 (1992).
Ozaki et al., Synthesis of Chiral Square Planar Cobalt (III) Complexes and Catalytic Asymmetric Epoxidations with these Complexes, J. Chem. Soc. Perkin Trans., 2 (1990).
Furuhashi, Production of Optically Active Epoxides by Microbial Oxidation of Olefins, Synthetic Organic Chemistry, Japan, 45 (2), 162 (1987).
Biological Abstracts, vol. BA91, Abstract No. 117835 (1991).
Chemical Abstracts, vol. 112, No. 9, Abstract No. 73537 (1990).
Chemical Abstracts, vol. 109, No. 11, Abstract No. 89364 (1988).

*Primary Examiner*—Sandra E. Saucier
*Attorney, Agent, or Firm*—Cushman Darby & Cushman IP Group of Pillsbury Madison & Sutro, LLP

[57] ABSTRACT

A microorganism or a preparation thereof is permitted to act on a mixture of enantiomers of an epoxide such as 3-chlorostyrene oxide and the product optically active epoxide is recovered. The microorganism able to produce an optically active (S)-epoxide from the mixture of enantiomers of the epoxide include, for example, a microorganism strain belonging to the genus Candida, the genus Rhodosporidium, the genus Rhodococcus and the genus Nosardioides. Examples of the microorganism capable of producing an optically active (R)-epoxide from said mixture include a microorganism strain belonging to the genus Trichosporon, the genus Geotrichum, the genus Corynebacterium, the genus Micrococcus and the genus Brevibacterium. The objective optically active epoxide can efficiently be obtained with ease and simplicity from the corresponding mixture of enantiomers of the epoxide.

10 Claims, No Drawings

PROCESS FOR ENRICHING AN [R,S]-1,2-EPOXIDE IN ONE ENANTIOMER BY USING MICROBES TO CONVERT ONE ENANTIOMER TO THE OTHER OR TO PREFERENTIALLY OPEN THE EPOXIDE RING

This is a continuation of application Ser. No. 08/195,080, filed on Feb. 14, 1994, which is now abandoned.

FIELD OF THE INVENTION

The present invention relates to a process for producing an optically active epoxide with the use of a microorganism. Such optically active epoxides are important intermediates for the synthesis of various medicinal compounds, optically active biologically active substances and derivatives thereof.

BACKGROUND OF THE INVENTION

For the production of an optically active epoxide, there are known chemical asymmetric epoxidation (J. Chem. Soc., Perkin Trans., 2, 353 (1990), etc.) and a technique with the aid of a microorganism (Journal of Synthetic Organic Chemistry, Japan, 45, (2), 162 (1987), etc.), from the corresponding olefin. These techniques, however, are not fully satisfactory in economical factors, handling efficiency, yield or other factors. Under the circumstances, the establishment of an economical and expedient process for production of an optically active epoxide has been demanded.

SUMMARY OF THE INVENTION

Accordingly, it is an object of the present invention to provide a process for producing an optically active epoxide efficiently with an simple and easy manner.

It is another object of the invention to provide a commercially useful process for producing an optically active epoxide having a higher optical purity.

A still another object of the present invention is to provide a process for increasing the optical purity of an optically active (S)- or (R)-epoxide efficiently with simple and easy manner.

The present inventors were interested in a process for the economical and expedient (simple and easy) production of an optically active epoxide having a higher optical purity and, after extensive researches, found that an optically active (S)- or (R)-epoxide having a higher optical purity can efficiently be obtained by permitting a microorganism or a preparation thereof to act on a mixture of enantiomers of an epoxide. The present invention has been accomplished on the basis of the above findings.

Thus, the present invention provides a process for producing an optically active epoxide which comprises:

permitting a microorganism capable of producing an optically active epoxide from a mixture of enantiomers of an epoxide shown by the general formula (I)

(I)

wherein R represents an optionally substituted alkyl group, an optionally substituted alkenyl group, an optionally substituted cycloalkyl group, an optionally substituted aryl group, an optionally substituted aralkyl group or an optionally substituted heterocyclic group, or a preparation thereof to act on said mixture of enantiomers of the epoxide; and recovering the product optically active epoxide.

The present invention also provides a process for increasing the optical purity of an optically active epoxide which comprises:

permitting (1) a microorganism that is capable of selectively or relatively decreasing the proportion of an (R)-enantiomer or converting the (R)-enantiomer to an (S)-enantiomer in said mixture of enantiomers of the epoxide shown by the general formula (I), or preparation thereof, or (2) a microorganism that is capable of selectively or relatively decreasing the proportion of the (S)-enantiomer or converting the (S)-enantiomer to the (R)-enantiomer in said mixture of enantiomers of the epoxide to act on said mixture of enantiomers of the epoxide; and increasing the optical purity of the (S)- or the (R)-epoxide.

The microorganisms to be employed in accordance with the invention may be any strain of microorganism able to produce an optically active epoxide from the mixture of enantiomers of the epoxide shown by the general formula (I). With the use of such strain of microorganism, the optical purity of the optically active (S)- or (R)-epoxide can efficiently be increased.

DETAILED DESCRIPTION OF THE INVENTION

Examples of the alkyl group represented by R include a straight chain or branched alkyl group having 1 to 12 carbon atoms such as methyl group, ethyl group, propyl group, isopropyl group, butyl group, isobutyl group, s-butyl group, t-butyl group, pentyl group, isopentyl group, hexyl group, isohexyl group, heptyl group, octyl group, nonyl group, decyl group, dodecyl group and the like. Typical examples of the alkyl group include a straight chain or branched alkyl group having 1 to 10 carbon atoms, especially a straight chain or branched alkyl group having 1 to 6 carbon atoms.

Examples of the alkenyl group represented by R include a straight chain or branched alkenyl group having 2 to 12 carbon atoms such as vinyl group, allyl group, 1-propenyl group, isopropenyl group, 1-butenyl group, 2-butenyl group, 3-butenyl group, 2-methyl-1-propenyl group, 4-pentenyl group, 5-hexenyl group, 7-octenyl group, 9-decenyl group and the like. Practically preferred examples of the alkenyl group include a straight chain or branched alkenyl group having 2 to 6 carbon atoms. A straight chain or branched alkenyl group having 2 to 4 carbon atoms or the like can advantageously be employed as the alkenyl group.

The cycloalkyl group represented by R is exemplified as a cycloalkyl group having 3 to 10 carbon atoms such as cyclopropyl group, cyclobutyl group, cyclopentyl group, cyclohexyl group, cycloheptyl group, cyclooctyl group and so on. Typical examples of the cycloalkyl group include, among others, a cycloalkyl group having 3 to 8 carbon atoms, and specifically preferred is a cycloalkyl group having 5 to 7 carbon atoms.

As examples of the aryl group represented by R, there may be mentioned phenyl group, naphthyl group and the like. Practically preferred examples of the aryl group include phenyl group.

Examples of the aralkyl group shown by R include an aralkyl group having 7 to 18 carbon atoms such as benzyl group, 1-methylbenzyl group, 2-phenylethyl group, 3-phenylpropyl group, 4-phenylbutyl group, 5-phenylpentyl group, 6-phenylhexyl group, 1-naphthylmethyl group, 2-naphthylmethyl group, 2-(1-naphthyl)ethyl group, etc. As preferred examples of the aralkyl group, there may be mentioned an aralkyl group having 7 to 12 carbon atoms such as benzyl group, 1-methylbenzyl group, 2-phenylethyl group, 3-phenylpropyl group, 4-phenylbutyl group, 1-naphthylmethyl group and 2-naphthylmethyl group.

As the heterocyclic group represented by R, there may be mentioned, for instance, a 5- to 7-membered heterocyclic group containing nitrogen, oxygen or sulfur atom. Said heterocyclic ring may be condensed with a carbocyclic ring having 3 to 7 carbon atoms such as benzene ring, cyclopentane ring and cyclohexane ring. Examples of the heterocyclic group include 3-furyl group, furfuryl group, 3-thienyl group, 3-pyrrolyl group, 3-pyrolidinyl group, 2-pyridyl group, 3-pyridyl group, 4-pyridyl group, 3-piperidinyl group, 4-piperidinyl group, 2-morpholinyl group, 2-quinolyl group, 3-quinolyl group, 6-quinolyl group, 4-isoquinolyl group, 4-oxazolyl group, 4-isooxazolyl group, 4-thiazolyl group, 1-imidazolyl group, 4-imidazolyl group, 4-pyrazolyl group, 2-pyrazinyl group, 5-pyrimidinyl group, 4-pyridazinyl group, 5-quinazolinyl group, 3-benzofuranyl group, 1-(2-pyrrolidonyl) group, 9-carbazolyl group, etc.

The alkyl group, alkenyl group, cycloalkyl group, aryl group, aralkyl group and heterocyclic group mentioned above may have a substituent. Examples of the substituent include a halogen atom (fluorine, chlorine, bromine, iodine atom), hydroxyl group, mercapto group, a substituted or unsubstituted amino group (e.g. amino, methylamino, dimethylamino, ethylamino, diethylamino group, etc.), nitro group, an alkoxy group (for example, an alkoxy group having 1 to 8 carbon atoms such as methoxy, ethoxy, propoxy, isopropoxy, butoxy, isobutoxy, t-butoxy, pentyloxy, hexyloxy and octyloxy group), an alkenyloxy group (for instance, an alkenyloxy group having 2 to 8 carbon atoms such as vinyloxy, allyloxy, 3-butenyloxy and 5-hexenyloxy group), an aryloxy group (e.g. phenoxy group or naphthyloxy group which may optionally be substituted with an alkyl group having 1 to 4 carbon atoms, an alkoxy group having 1 to 4 carbon atoms, a halogen atom, etc., including phenoxy, 2-methylphenoxy, 3-methylphenoxy, 4-methylphenoxy, 2-allylphenoxy, 2-chlorophenoxy, 3-chlorophenoxy, 4-chlorophenoxy, 4-methoxyphenoxy, 2-allyloxyphenoxy, α-naphthyloxy group and the like), an aralkyloxy group (e.g. an aralkyloxy group having 7 to 18 carbon atoms such as benzyloxy and 2-phenylethyloxy group), an alkylthio group (for example, an alkylthio group having 1 to 8 carbon atoms such as methylthio, ethylthio, propylthio and isobutylthio group), carboxyl group, an alkoxycarbonyl group (for instance, an alkoxycarbonyl group having 2 to 6 carbon atoms such as methoxycarbonyl, ethoxycarbonyl group, etc.), a substituted or unsubstituted carbamoyl group such as carbamoyl, methylcarbamoyl, dimethylcarbamoyl, and diethylcarbamoyl group), cyano group, an acyl group (e.g. an acyl group having 1 to 10 carbon atoms such as formyl, acetyl, propionyl and benzoyl group), and others.

The above-mentioned cycloalkyl group, aryl group, aralkyl group and heterocyclic group may also be substituted with, as well as the substituent as above, an alkyl group (for instance, an alkyl group having 1 to 5 carbon atoms such as methyl, ethyl, propyl, isopropyl and butyl group), an alkenyl group (e.g. an alkenyl group having 2 to 5 carbon atoms such as vinyl group and allyl group, etc.) a haloalkyl group (for example, a haloalkyl group having 1 to 5 carbon atoms including chloromethyl, 2-chloroethyl, trifluoromethyl, 1,1,2,2,2-pentafluoroethyl group and the like).

As preferred examples of the substituent for the alkyl group and the alkenyl group, there may be mentioned hydroxyl group; an alkoxy group having 1 to 8 carbon atoms; an alkenyloxy group having 2 to 8 carbon atoms; an aryloxy group optionally having a substituent such as an alkyl group having 1 to 4 carbon atoms, an alkoxy group having 1 to 4 carbon atoms and a halogen atom; and an aralkyloxy group having 7 to 18 carbon atoms.

Typical examples of the substituent for the cycloalkyl group, aryl group, aralkyl group and heterocyclic group include a halogen atom, an alkoxy group having 1 to 5 carbon atoms, an alkyl group having 1 to 5 carbon atoms, a haloalkyl group having 1 to 5 carbon atoms, and nitro group, and among them, a halogen atom such as chlorine atom can advantageously be employed.

The number of the substituent(s) may be 1, or 2 or more, and in the latter case, said substituents may be the same or different.

Among the above mentioned groups represented by R, typically preferred is the aryl group such as phenyl group which may optionally be substituted with a halogen atom, an alkoxy group having 1 to 5 carbon atoms, an alkyl group having 1 to 5 carbon atoms, a haloalkyl group having 1 to 5 carbon atoms, nitro group or the like. Phenyl group optically substituted with a halogen atom or the like can advantageously be used as the group represented by R. The epoxides having such group as R are extremely useful as synthetic intermediates for obtaining an anti-diabetic agent, anti-obesity agent or others (see J. Med. Chem., 35, 3081 (1992), and U.S. Pat. No. 5,061,727, etc.).

The epoxide shown by the formula (I) is classified into following categories; (1) a compound wherein R is an optionally substituted alkyl group; (2) a compound wherein R is an optionally substituted alkenyl group; (3) a compound wherein R is an optionally substituted cycloalkyl group; (4) a compound wherein R is an optionally substituted aryl group; (5) a compound wherein R is an optionally substituted aralkyl group; and (6) a compound wherein R is an optionally substituted heterocyclic compound.

As the compound included in said category (1), there may be mentioned, for instance, 1,2-epoxyalkanes such as 1,2-epoxypropane, 1,2-epoxybutane, 1,2-epoxy-3-methylbutane, 1,2-epoxypentane, 1,2-epoxyhexane, 1,2-epoxyheptane and 1,2-epoxydecane; 1,2-epoxyalkanols such as glycidol, 1,2-epoxy-4-hydroxybutane and 1,2-epoxy-5-hydroxypentane; glycidyl ethers such as methyl glycidyl ether, ethyl glycidyl ether, propyl glycidyl ether, butyl glycidyl ether, vinyl glycidyl ether, allyl glycidyl ether, phenyl glycidyl ether, o-methyl-phenyl glycidyl ether, m-methylphenyl glycidyl ether, p-methylphenyl glycidyl ether, o-allylphenyl glycidyl ether, o-allyloxyphenyl glycidyl ether, benzyl glycidyl ether and α-naphthyl glycidyl ether.

Examples of the compound contained in said category (2) include epoxyalkenes such as 3,4-epoxy-1-butene, 4,5-epoxy-1-pentene, 4,5-epoxy-2-pentene, 5,6-epoxy-1-hexene and 7,8-epoxy-1-octene.

As the compound included in the category (3), there may be mentioned, for instance, 2-cycloalkyloxiranes such as 2-cyclopropyloxirane, 2-cyclopentyloxirane, 2-cyclohexyloxirane and 2-cycloheptyloxirane.

The compounds included in the category (4) are exemplified as styrene oxide, styrene oxides having a substituent in the benzene ring including, for example, styrene oxides having a halogen atom in the benzene ring such as 2-chlorostyrene oxide, 3-fluorostyrene oxide, 3-chlorostyrene oxide, 3-bromostyrene oxide, chlorostyrene oxide, 2,3-difluorostyrene oxide, 2,3-dichlorostyrene oxide, 3-chloro-2-methylstyrene oxide, 2,4-dichlorostyrene oxide, 2,5-dichlorostyrene oxide, 2,6-dichlorostyrene oxide, 3,4-difluorostyrene oxide, 3,4-dichlorostyrene oxide, 3,5-dichlorostyrene oxide, 2,3,4-trifluorostyrene oxide, 2,3,4-trichlorostyrene oxide, 2,3,5-trichlorostyrene oxide, 2,3,6-trichlorostyrene oxide, 2,4,5-trichlorostyrene oxide, 2,4,6-trichlorostyrene oxide, 3,4,5-trichlorostyrene oxide, 2,3,4,5-tetrachlorostyrene oxide, 2,3,4,6-tetrachlorostyrene oxide, 2,3,5,6-tetrachlorostyrene oxide and 2,3,4,5,6-pentachlorostyrene oxide; styrene oxides having an alkyl group of 1 to 5 carbon atoms in the benzene ring such as 2-methylstyrene oxide, 3-methylstyrene oxide, 4-methylstyrene oxide and 4-t-butylstyrene oxide; styrene oxides having a haloalkyl group of 1 to 5 carbon atoms in the benzene ring such as 2-chloromethylstyrene oxide and 3-trifluoromethylstyrene oxide; styrene oxides having an alkoxy group of 1 to 5 carbon atoms in the benzene ring such as 2-methoxystyrene oxide, 3-methoxystyrene oxide and 4-ethoxystyrene oxide; and 3-nitrostyrene oxide, and 1,2-epoxy-2-naphthylethanes such as 1,2-epoxy-2-(1-naphthyl) ethane and 1,2-epoxy-2-(2-naphthyl)ethane. Styrene oxide and styrene oxides having 1 to 5 halogen atoms can advantageously be used among the compounds included in the category (4).

As the compounds included in the category (5), there may be mentioned, for example, epoxyalkylarenes such as 2,3-epoxypropylbenzene, 1-(2,3-epoxypropyl)-2-methylbenzene, 1-chloro-3-(2,3-epoxypropyl)benzene, 3,4-epoxybutylbenzene, 1-chloro-3-(3,4-epoxybutyl)benzene, 4,5-epoxypentylbenzene, 5,6-epoxyhexylbenzene, 1-(2,3-epoxypropyl)naphthalene, 2-(2,3-epoxypropyl)naphthalene and 1-(3,4-epoxybutyl)naphthalene.

The compound included in the category (6) is exemplified as 3-(2-oxiranyl)furan, 3-(2-oxiranyl)pyrrole, 2-(2-oxiranyl) pyridine, 3-(2-oxiranyl)pyridine, 4-(2-oxiranyl)pyridine, 6-(2-oxiranyl)quinoline, 1-(2-oxiranyl)imidazole, 1-(2-oxiranyl)-2-pyrrolidone, 3-(2-oxiranyl)piperidine, 2-(2-oxiranyl)pyrazine, 2-(2-oxiranyl)quinoline, 9-(2-oxiranyl) carbazole and the like.

The microorganisms to be employed in accordance with the invention may be any strain of microorganisms able to produce an optically active epoxide from a mixture of enantiomers of the epoxide shown by the general formula (I). Such microorganism includes a microorganism capable of selectively or relatively utilizing or decreasing one enantiomer by, for example, ring-opening of the epoxy ring, and a microorganism capable of selectively or relatively converting one enantiomer to other compound (including the other enantiomer).

Examples of the microorganisms having the capability or ability just mentioned above include those microorganisms which are able to act on the mixture of enantiomers of the epoxide shown by the general formula (I) to produce an optically active (S)-epoxide, for example, strains of microorganisms selected from the group of microorganisms belonging to the genus Candida, the genus Rhodosporidium, the genus Rhodococcus, the genus Serratia, the genus Aspergillus, the genus Nocardioides, the genus Saccharopolyspora, the genus Bacillus, the genus Acetobacter, the genus Citrobacter, the genus Enterobacter, the genus Escherichia, the genus Micrococcus, the genus Pseudomonas, the genus Gluconobacter, the genus Streptoallotichus, the genus Anixiella, the genus Corticium, the genus Coryonespora, the genus Doratomyces, the genus Drechslera, the genus Helminthosporium, the genus Macrophomina, the genus Microascus, the genus Periconia, the genus Scopulariopsis, the genus Stachybotrys, the genus Westerdykella, the genus Phialophora, the genus Podospora, the genus Tilletiopsis and the genus Gloeophyllum, that are able to produce an optically active (S)-epoxide from said mixture of enantiomers of the epoxide shown by the general formula (I); and those microorganisms which are able to act on a mixture of enantiomers of an epoxide shown by the general formula (I) to produce an optically active (R)-epoxide, for example, strains of microorganisms selected from the group of microorganisms belonging to the genus Trichosporon, the genus Geotrichum, the genus Bacillus, the genus Corynebacterium, the genus Micrococcus, the genus Brevibacterium, the genus Pseudomonas, the genus Serratia, the genus Aspergillus, the genus Glycomyces, the genus Saccharothrix, the genus Streptomyces and the genus Pellicularia, that are able to produce an optically active (R)-epoxide from said mixture of enantiomers of the epoxide shown by the general formula (I).

As typical examples of the strain of microorganisms that is able to act on the mixture of enantiomers of the epoxide shown by the general formula (I) to produce an optically active (S)-epoxide, there may be mentioned
(1) the genus Candida: *Candida parapsilosis* IFO 1068, *Candida famata* IFO 0856, etc.,
(2) the genus Rhodosporidium: *Rhodosporidium toruloides* IFO 1535, etc.,
(3) the genus Rhodococcus: *Rhodococcus rubropertinctus* IFM 0033, *Rhodococcus coprophilus* IFM 0143, *Rhodococcus erythropolis* JCM 6823, etc.,
(4) the genus Serratia: *Serratia plymuthica* IFO 3055, *Serratia marcescens* AHU 1720, etc.,
(5) the genus Aspergillus: *Aspergillus niger* ATCC 6275, etc.,
(6) the genus Nocardioides: *Nocardioides flavus* IFO 96, etc.,
(7) the genus Saccharopolyspora: *Saccharopolyspora hirsuta* IFO 13919, etc.,
(8) the genus Bacillus: *Bacillus subtilis* IFO 3108, *Bacillus cereus* AHU 1355, etc.,
(9) the genus Acetobacter: *Acetobacter pasteurianus* ATCC 10245, *Acetobacter aceti* subsp. xylinum IFO 3288, etc.,
(10) the genus Citrobacter: *Citrobacter freundii* AHU 534, etc.,
(11) the genus Enterobacter: *Enterobacter aerogenes* AHU 1340, *Enterobacter cloacae* IAM 1615, etc.,
(12) the genus Escherichia: *Escherichia coli* AHU 1520, etc.,
(13) the genus Micrococcus: *Micrococcus luteus* AHU 1427, etc.,
(14) the genus Pseudomonas: *Pseudomonas putida* IFO 3738, etc.,
(15) the genus Gluconobacter: *Gluconobacter cerinus* IFO 3264, etc.,
(16) the genus Streptoallotichus: *Streptoallotichus hindustanus* IFO 14056, etc.,
(17) the genus Anixiella: *Anixiella reticulata* IFO 5814, etc.,
(18) the genus Corticium: *Corticium rolfsii* IFO 4476, etc.,
(19) the genus Corynspora: *Corynspora cassiicola* IFO 6724, etc.,
(20) the genus Doratomyces: *Doratomyces stemonitis* IFO 5878, etc.,
(21) the genus Drechslera: *Drechslera avenae* IFO 6636, etc.,
(22) the genus Helminthosporium: *Helminthosporium sigmoideum* var. irregul IFO 5273, etc.,
(23) the genus Macrophomina: *Macrophomina phaseoli* IFO 6696, etc.,
(24) the genus Microascus: *Microascus desmosporus* IFO 6761, etc.,

(25) the genus Periconia: *Periconia byssoides* IFO 9444, etc.,

(26) the genus Scopulariopsis: *Scopulariopsis brevicaulis* IFO 4843, etc.,

(27) the genus Stachybotrys: *Stachybotrys chartatum* IFO 5369, etc.,

(28) the genus Westerdykella: *Westerdykella multispora* IFO 5813, etc.,

(29) the genus Phialophora: *Phialophora pedrosoi* IFO 6071, etc., (30) the genus Podospora: *Podospora cardonaria* IFO 30294, etc.,

(31) the genus Tilletiopsis: *Tilletiopsis cremea* IFO 6831, etc., and

(32) the genus Gloeophyllum: *Gloeophyllum striatum* IFO 6506, etc.

At least one strain of these microorganisms can be employed. By means of permitting or allowing the microorganism or a preparation thereof to act on a mixture of enantiomers of an epoxide shown by the general formula (I), the amount or proportion of (R)-form in the both enantiomers can selectively or relatively be decreased (lessened) with (S)-form selectively being left or the (R)-form can selectively or relatively be converted to other compound including the (S)-form, thus the optical purity of said (S)-form can be increased. Therefore, the objective optically active (S)-epoxide can efficiently be obtained with a higher yield by use of said microorganism.

Practical examples of the strain of microorganism that is able to act on a mixture of enantiomers of an epoxide shown by the general formula (I) to produce an optically active (R)-epoxide include

(33) the genus Trichosporon: *Trichosporon cutaneum* IFO 1198, etc.,

(34) the genus Geotrichum: *Geotrichum candidum* JCM 7389, *Geotrichum fragrans* JCM 2450, etc.,

(35) the genus Bacillus: *Bacillus sphaericus* IFO 3341, etc.,

(36) the genus Corynebacterium: *Corynebacterium glutamicum* ATCC 13032, etc.,

(37) the genus Micrococcus: *Micrococcus luteus* IFO 12992, etc.,

(38) the genus Brevibacterium: *Brevibacterium linens* IFO 12141, etc.,

(39) the genus Pseudomonas: *Pseudomonas aeruginosa* IFO 3452, etc.,

(40) the genus Serratia: *Serratia marcescens* IAM 1105, etc.,

(41) the genus Aspergillus: *Aspergillus oryzae* var. *magnasporus* IAM 2750, *Aspergillus sojae* IAM 2631, etc.,

(42) the genus Glycomyces: *Glycomyces rutgersensis* IFO 14488, etc.,

(43) the genus Saccharothrix: *Saccharothrix australiensis* IFO 14444, etc.,

(44) the genus Streptomyces: *Streptomyces albosporeus* HUT 6130, etc., and

(45) the genus Pellicularia: *Pellicularia filamentosa* IFO 6254, etc.

At least one strain of these microorganisms can be employed. By means of permitting or allowing the microorganism or a preparation thereof to act on a mixture of enantiomers of an epoxide shown by the general formula (I), the proportion of (S)-form in the both enantiomers can selectively or relatively be decreased (lessened) so as to selectively leave the (R)-form, or the (S)-form can selectively or relatively be converted to other compound including the (R)-form, thus the optical purity of said (R)-form can be increased. Therefore, the efficient production of the objective optically active (R)-epoxide with a higher yield can be achieved by use of said microorganism.

The microorganisms identified hereinabove by IFO numbers are described in the "List of Cultures Ed. 8, (1988)" published by Institute for Fermentation, Osaka (IFO), Japan and are available from the same Institute. The microorganisms designated by JCM numbers are listed in "Catalogs of Microbial Strains Ed. 4 (1989)" published by the Culture Collection of The Institute of Physical and Chemical Research, Japan and available from the same Culture Collection. The microorganisms designated by ATCC numbers are listed in "Catalogue of Bacteria Phages rDNA Vectors, Ed. 16 (1985)" and "Catalogue of Fungi/Yeast, Ed. 17 (1987)" each published by the American Type Culture Collection (ATCC) and are available from the same organization. The microorganisms identified by AHU numbers are listed in "Catalogue of cultures, Ed. 5 (1992)" published by Japan Federation of Culture Collections (JFCC) and are available from Faculty of Agriculture, Hokkaido University, Japan. The microorganisms titled by IAM numbers are available from Institute of Applied Microbiology, Tokyo University, Japan and the microorganisms identified by IFM numbers and HUT numbers are respectively available from Chiba University, Japan and Hiroshima University, Japan.

For the purposes of the invention, any of wild strains, mutants and recombinant strains which can be obtained by a genetic engineering technique such as cell fusion or gene manipulation, as far as being able to produce an optically active epoxide from a mixture of enantiomers of the epoxide shown by the formula (I), can advantageously be employed.

A microorganism, such as the above, is usually grown in a culture medium and, then, submitted to the reaction with a mixture of enantiomers of the epoxide shown by the general formula (I).

The medium which is used for growing the strain for use in the invention is not critical in composition only if the selected strain may grow and multiply therein. The medium may frequently be a fluid medium containing sources of carbon and nitrogen and other nutrients. Any carbon source which the strain can utilize may be employed. As the sources of carbon, there may be employed various carbohydrates or saccharides such as glucose, fructose, sucrose, dextrin, starch, etc.; alcohols such as sorbitol, methanol, ethanol, glycerol, etc.; organic acids such as fumaric acid, citric acid, acetic acid, propionic acid, etc. and the corresponding salts; hydrocarbons such as paraffin; and various mixtures thereof. The sources of nitrogen include, among others, inorganic acid ammonium salts such as ammonium chloride, ammonium sulfate, ammonium phosphate, etc.; organic acid ammonium salts such as ammonium fumarate, ammonium citrate, etc.; inorganic or organic nitrogen-containing materials such as meat extract, yeast extract, malt extract, peptone (polypeptone), corn steep liquor, casein hydrolysate, urea, etc.; and various mixtures thereof.

In the medium, there may be incorporated appropriate amounts of those nutrients which are commonly employed in the cultivation of microorganisms, such as inorganic salts, trace metal salts and vitamins. Where necessary, there may also be incorporated factors which may promote growth of the strain used and/or factors which may augment its ability to produce the object compound of the invention, such as an epoxide shown by the general formula (I), as well as a buffer substance which may assist in the maintenance of the medium at a given pH.

The cultivation of the microorganism is carried out under conditions optimal for the growth of the particular strain, for example at a medium pH in the range of about 3.0 to 9.5, preferably about 4 to 8, and an incubation temperature in the range of about 20 to 45° C., preferably about 25° to 37° C.

The cultivation may be aerobic or anaerobic. The cultivation time may, for example, be 5 to 120 hours, preferably about 12 to 72 hours.

The proportions of (R) and (S) in the substrate mixture of enantiomers of an epoxide shown by the formula (I) are not critical but it is advantageous for commercial purpose to employ a racemic form of the epoxide shown by the general formula (I).

The method of production of an optically active epoxide from a mixture of enantiomers of the corresponding epoxide shown by the general formula (I) may, for example, be whichever of the following alternatives: (1) a technique which comprises mixing or blending a mixture of enantiomers of said epoxide with a culture broth as such to conduct the reaction, (2) a technique which comprises separating the microbial cells from the culture broth, e.g. by centrifugation, resuspending the cells, either as they are or after washing, in a buffer solution, water or the like, and adding a mixture of enantiomers of the epoxide to the resulting cell suspension to treat the mixture therewith, (3) a technique which comprises using not viable cells but a treated preparation of cells such as disrupted cells, acetone-treated cells, lyophilized cells and so on and blending or mixing a mixture of enantiomers of the epoxide to the resulting cell preparation to conduct the reaction, and (4) a technique which comprises immobilizing these cells or preparations thereof by known techniques such as the polyacrylamide gel method, sulfur-containing polysaccharide gel method (e.g. carrageenin gel method), alginic acid gel method, agar gel method and so on and treating said mixture of enantiomers of the epoxide therewith. The enzyme purified from such a cell preparation can also be employed. The enzyme can be obtained with the use of known purification processes in a suitable combination.

There are cases in which this reaction proceeds with advantage of a higher yield of the objective optically active epoxide in the presence of a carbon source such as glucose, sucrose, ethanol, methanol or paraffin which serves as an energy source.

The corresponding mixture of enantiomers of the epoxide can be used as it is or in the form of a solution, suspension or dispersion containing a suitable solvent. As the solvent, water or an organic solvent which will not interfere with the reaction can be employed. A suspension or a dispersion prepared with a surfactant can also be used when necessary. The mixture of enantiomers of the epoxide may be added in bolus at the beginning of the reaction or in several installments.

The optimal cell concentration of the reaction system can be selected from the range where the optical purity and the efficiency of producing the desired optically active compound intact will not be adversely affected. A typical cell concentration may for example be, on a dry cell basis, about 0.1 to 100 g/liter and preferably about 1 to 50 g/liter. The concentration of substance mixture of enantiomers of the epoxide is not particularly restricted and is, for example, about 0.1 to 20% by weight and preferably about 0.2 to 10% by weight.

The reaction conditions can be selected from the ranges that will not detract from the yield of the object compound. For example, the pH of the reaction system can be selected from the range of pH about 3 to 9 and preferably pH about 4 to 8. The reaction temperature is selected from the range of, for example, about 10° to 60° C. and preferably from about 20° to 40° C. The reaction can be conducted with stirring or under stationary conditions for about 1 to 120 hours. As a tendency, the longer the reaction time, the higher is the optical purity of the desired compound.

The optically active epoxide produced by the reaction can be recovered or harvested by the separation and purification procedures generally known. For example, the optically active epoxide can be easily obtained by subjecting the reaction mixture, directly or after separation of the cells, to the conventional purification procedure such as membrane separation, extraction with an organic solvent such as hexane, chloroform and ethyl acetate, column chromatography, vacuum concentration and distillation. The optical purity of optically active epoxide can be measured by high performance liquid chromatography (HPLC) using an optical resolution column.

Thus, according to the method of the present invention with the aid of a microorganism or preparation thereof, an optically active epoxide can efficiently be produced with simple and easy manner, further an optically active epoxide of a higher optical purity can be produced with commercial advantages.

The following examples are intended to illustrate the invention in further detail and should by no means be construed as delimiting the scope of the invention.

EXAMPLES

In the examples, the quantitative determination of each epoxide in reaction mixture was carried out by subjecting the epoxide to gas chromatography using a column (column: Thermon 3000, Chromosorb W; length: 2 m; the column temperature: 140° C.). The optical purity determination thereof was carried out by subjecting the reaction mixture to extraction with n-hexane, then the resultant extract (n-hexane extract) to high performance liquid chromatography using an optical resolution column (column: Chiralcel OB (trade name), Daicel Chemical Industries, Ltd.; moving phase: n-hexane/isopropyl alcohol=99.9/0.1; wavelength: 254 nm; flow rate: 1 ml/min.).

Example 1 to 54

The following cell-preparing media (1) and (2) were prepared:

| Cell-preparing medium (1) for a yeast | |
|---|---|
| Glucose | 2.0 weight % |
| Yeast extract | 0.3 weight % |
| Malt extract | 0.3 weight % |
| Polypeptone | 0.5 weight % |
| Deionized water (pH 6.0) | 96.9 weight % |
| Cell-preparing medium (2) for a bacterium | |
| Glucose | 2.0 weight % |
| Yeast extract | 0.5 weight % |
| Meat extract | 0.3 weight % |
| Polypeptone | 0.3 weight % |
| Ammonium sulfate | 0.2 weight % |
| Potassium dihydrogen-phosphate | 0.1 weight % |
| Deionized water (pH 7.0) | 96.6 weight % |

A test tube of inner diameter of 21 mm φ was charged with 5 ml of the cell-preparing medium as above. After sterilization, the tube was inoculated with one of the following microbial stains. The medium (1) was used for a yeast and the medium (2) was employed for a bacterium respectively. The inoculated tube was incubated under shaking at 30° C. for 48 hours. Subsequently, cells were isolated by centrifuging to obtain viable cells.

Example 1
*Candida parapsilosis* IFO 1068,

Example 2
*Candida famata* IFO 0856,

Example 3
*Rhodosporidium toruloides* IFO 1535,

Example 4
*Rhodococcus rubropertinctus* IFM 0033,

Example 5
*Rhodococcus coprophilus* IFM 0143,

Example 6
*Rhodococcus erythropolis* JCM 6823,

Example 7
*Serratia plymuthica* IFO 3055,

Example 8
*Serratia marcescens* AHU 1720,

Example 9
*Aspergillus niger* ATCC 6275,

Example 10
*Nocardioides flavus* IFO 14396,

Example 11
*Saccharopolyspora hirsuta* IFO 13919,

Example 12
*Bacillus subtilis* IFO 3108,

Example 13
*Bacillus cereus* AHU 1355,

Example 14
*Acetobacter pasteurianus* ATCC 10245,

Example 15
*Acetobacter aceti* subsp. *xylinum* IFO 3288,

Example 16
*Citrobacter freundii* AHU 1534,

Example 17
*Enterobacter aerogenes* AHU 1340,

Example 18
*Enterobacter cloacae* IAM 1615,

Example 19
*Escherichia coli* AHU 1520,

Example 20
*Micrococcus luteus* AHU 1427,

Example 21
*Pseudomonas putida* IFO 3738,

Example 22
*Gluconobacter cerinus* IFO 3264,

Example 23
*Streptoallotichus hindustanus* IFO 14056,

Example 24
*Anixiella reticulata* IFO 5814,

Example 25
*Corticium rolfsii* IFO 4476,

Example 26
*Corynespora cassiicola* IFO 6724,

Example 27
*Doratomyces stemonitis* IFO 5878,

Example 28
*Drechslera avenae* IFO 6636,

Example 29
*Helminthosporium sigmoideum* var. *irregul* IFO 5273,

Example 30
*Macrophomina phaseoli* IFO 6696,

Example 31
*Microascus desmosporus* IFO 6761,

Example 32
*Periconia byssoides* IFO 9444,

Example 33
*Scopulariopsis brevicaulis* IFO 4843,

Example 34
*Stachybotrys chartatum* IFO 5369,

Example 35
*Westerdykella multispora* IFO 5813,

Example 36
*Phialophora pedrosoi* IFO 6071,

Example 37
*Podospora cardonaria* IFO 30294,

Example 38
*Tilletiopsis cremea* IFO 6831,

Example 39
*Gloeophyllum striatum* IFO 6506,

Example 40
*Trichosporon cutaneum* IFO 1198,

Example 41

*Geotrichum candidum* JCM 7389,

Example 42

*Geotrichum fragrans* JCM 2450,

Example 43

*Bacillus sphaericus* IFO 3341,

Example 44

*Corynebacterium glutamicum* ATCC 13032,

Example 45

*Micrococcus luteus* IFO 12992,

Example 46

*Brevibacterium linens* IFO 12141,

Example 47

*Pseudomonas aeruginosa* IFO 3452,

Example 48

*Serratia marcescens* IAM 1105,

Example 49

*Aspergillus oryzae* var. *magnasporus* IAM 2750,

Example 50

*Aspergillus sojae* IAM 2631,

Example 51

*Glycomyces rutgersensis* IFO 14488,

Example 52

*Saccharothrix australiensis* IFO 14444,

Example 53

*Streptomyces albosporeus* HUT 6130, and

Example 54

*Pellicularia filamentosa* IFO 6254.

A test tube of inner diameter of 21 mm φ was charged with 2.5 ml of 0.1M potassium phosphate buffer (pH 7.0) and said viable cells (in a concentration of about 10 to 30 mg/ml on a dry cell basis) were suspended therein. To the suspension was added 12.5 μl of racemic 3-chlorostyrene oxide, and the reaction was conducted on a reciprocating shaker at 30° C. for 48 hours.

After completion of the reaction, 1 ml of the reaction suspension was extracted with 2 ml of n-hexane. The n-hexane extract was subjected to gas chromatography to determine the amount of the remained or residual 3-chlorostyrene oxide.

The n-hexane extract was subjected to the determination of the absolute configuration and optical purity of the optically active 3-chlorostyrene oxide using high performance liquid chromatography. The results are set forth in Tables 1 to 3. In the Tables, the term "amount" refers to the amount of optically active 3-chlorostyrene oxide in the reaction mixture (mg/ml).

TABLE 1

| Example No. | Absolute configuration | Optical purity (% e.e.) | Amount (mg/ml) |
|---|---|---|---|
| 1 | S | 18 | 1.2 |
| 2 | S | 24 | 0.8 |
| 3 | S | 28 | 2.0 |
| 4 | S | 77 | 0.3 |
| 5 | S | 64 | 1.5 |
| 6 | S | 12 | 2.4 |
| 7 | S | 18 | 0.3 |
| 8 | S | 14.6 | 2.50 |
| 9 | S | 98 | 0.5 |
| 10 | S | 10.1 | 0.23 |
| 11 | S | 34.6 | 0.50 |
| 12 | S | 16.1 | 2.47 |
| 13 | S | 25.5 | 4.92 |
| 14 | S | 15.5 | 2.52 |
| 15 | S | 31.4 | 0.01 |
| 16 | S | 20.5 | 3.43 |
| 17 | S | 19.7 | 3.39 |
| 18 | S | 18.5 | 1.75 |
| 19 | S | 27.9 | 1.84 |
| 20 | S | 10.1 | 1.62 |

TABLE 2

| Example No. | Absolute configuration | Optical purity (% e.e.) | Amount (mg/ml) |
|---|---|---|---|
| 21 | S | 18.3 | 1.66 |
| 22 | S | 10.0 | 0.84 |
| 23 | S | 12.4 | 1.31 |
| 24 | S | 10.4 | 0.49 |
| 25 | S | 11.9 | 1.15 |
| 26 | S | 11.4 | 0.47 |
| 27 | S | 12.1 | 0.94 |
| 28 | S | 12.1 | 0.99 |
| 29 | S | 11.5 | 1.11 |
| 30 | S | 100.0 | 0.05 |
| 31 | S | 12.8 | 0.29 |
| 32 | S | 11.4 | 0.93 |
| 33 | S | 12.2 | 0.32 |
| 34 | S | 12.4 | 0.75 |
| 35 | S | 11.9 | 0.82 |
| 36 | S | 19.3 | 0.37 |
| 37 | S | 22.8 | 1.65 |
| 38 | S | 14.2 | 3.86 |
| 39 | S | 10.3 | 4.39 |

TABLE 3

| Example No. | Absolute configuration | Optical purity (% e.e.) | Amount (mg/ml) |
|---|---|---|---|
| 40 | R | 24 | 0.9 |
| 41 | R | 28 | 0.3 |
| 42 | R | 15 | 0.2 |
| 43 | R | 18 | 0.7 |
| 44 | R | 16 | 0.5 |
| 45 | R | 13 | 0.6 |
| 46 | R | 14 | 0.6 |
| 47 | R | 41 | 0.4 |
| 48 | R | 14 | 0.4 |
| 49 | R | 100 | 0.1 |
| 50 | R | 100 | 0.1 |
| 51 | R | 15.3 | 0.09 |
| 52 | R | 10.6 | 0.72 |
| 53 | R | 29.7 | 0.15 |
| 54 | R | 43.7 | 1.20 |

Examples 55 to 72

The procedures of Example 1 were repeated except for using the following substrates (each in racemic form) instead of 3-chlorostyrene oxide and employing the following microorganism strains A, B or C.

[Substrate]

Examples 55 to 57: glycidol,

Examples 58 to 60: allyl glycidyl ether,

Examples 61 to 63: 3,4-epoxy-1-butene,

Examples 64 to 66: 1,2-epoxyhexane,

Examples 67 to 69: 2,3-epoxypropylbenzene, and

Examples 70 to 72: styrene oxide

[Microorganism strain]

A: *Aspergillus oryzae* var. *magnasporus* IAM 2750,

B: *Aspergillus niger* ATCC 6275, and

C: *Rhodococcus rubropertinctus* IFM 0033

After completion of the reaction, the amount of each epoxide, the absolute configuration and the optical purity of the optically active epoxide were determined in the same manner as in Example 1. The results are shown in Table 4. In the Table, the term "amount" means the amount of the respective optically active epoxide in the reaction mixture (mg/ml).

TABLE 4

| Example No. | Micro-organism | Absolute configuration | Optical purity (% e.e.) | Amount (mg/ml) |
|---|---|---|---|---|
| 55 | A | R | 80 | 0.5 |
| 56 | B | S | 85 | 0.2 |
| 57 | C | S | 40 | 0.8 |
| 58 | A | R | 85 | 0.4 |
| 59 | B | S | 50 | 0.8 |
| 60 | C | S | 33 | 1.0 |
| 61 | A | R | 77 | 0.5 |
| 62 | B | S | 65 | 0.4 |
| 63 | C | S | 52 | 0.9 |
| 64 | A | R | 72 | 0.3 |
| 65 | B | S | 80 | 0.2 |
| 66 | C | S | 45 | 1.2 |
| 67 | A | R | 76 | 0.3 |
| 68 | B | S | 85 | 0.2 |
| 69 | C | S | 28 | 1.0 |
| 70 | A | R | 98 | 0.3 |
| 71 | B | S | 98 | 0.2 |
| 72 | C | S | 46 | 1.0 |

What is claimed is:

1. A process for enriching or preferentially increasing the concentration of the (S)-enantiomer of the epoxide of formula (I) in an enantiomeric mixture of (R,S)-epoxide of formula (I)

     (I)

comprising:

(a) adding a mixture of (R,S)-enantiomers of the epoxide of formula (I) to a microorganism or a preparation of said microorganism selected from the group consisting of *Candida parapsilosis*, *Candida famata*, *Rhodosporidium toruloides*, *Aspergillus niger*, *Nocardioides flavus*, *Saccharopolyspora hirsuta*, *Bacillus subtilis*, *Bacillus cereus*, *Acetobacter pasteurianus*, *Acetobacter aceti* subsp. *xylinum*, *Citrobacter freundii*, *Enterobacter aerogenes*, *Enterobacter cloacae*, *Escherichia coli*, *Pseudomonas putida*, *Gluconobacter cerinus*, *Streptoallotichus hindustanus*, *Anixiella reticulata*, *Corticium rolfsii*, *Corynespora cassiicola*, *Doratomyces stemonitis*, *Drechslera avenae*, *Helminthosporium sigmoideum* var. *irregul*, *Macrophomina phaseoli*, *Microascus desmosporus*, *Periconia byssoides*, *Scopulariopsis brevicaulis*, *Stachybotrys chartarum*, *Westerdykella multispora*, *Phialophora pedrosoi*, *Podospora cardonaria*, *Tilletiopsis cremea* and *Gloeophyllum striatum*, (b) allowing the microorganism or preparation of said microorganism to preferentially op an the epoxy ring of the (R)-enantiomer of formula (I) or to preferentially convert the (R)-enantiomer of formula (I) into the (S)-enantiomer of formula (I), and (c) recovering the (S)-enantiomer of formula (I), where R is an alkyl group, an alkenyl group, a cycloalkyl group, an aryl group, an aralkyl group or a heterocyclic group, said groups optionally having a substituent selected from the group consisting of (1) a halogen atom, (2) a hydroxyl group, (3) a mercapto group, (4) an amino group, (5) a nitro group, (6) an alkoxy group, (7) an alkenyloxy group, (8) a phenoxy group which may be substituted with (i) an alkyl group having 1–4 carbon atoms, (ii) an alkoxy group having 1–4 carbon atoms or (iii) a halogen atom, (9) a naphthyloxy group which may be substituted with (i) an alkyl group having 1–4 carbon atoms, (ii) an alkoxy group having 1–4 carbon atoms or (iii) a halogen atom, (10) an aralkyloxy group, (11) an alkyl-thio group, (12) a carboxyl group, (13) a carbamoyl group, (14) a cyano group, and (15) an acyl group, wherein said cycloalkyl group, aryl group, aralkyl group and heterocyclic group represented by R may also be substituted with (16) an alkyl group, (17) an alkenyl group or (18) a haloalkyl group.

2. A process for enriching or preferentially increasing the concentration of the (R)-enantomer of the epoxide of formula (I) in an enantiomeric mixture of (R,S)-epoxide of formula (I)

     (I)

comprising:

(a) adding a mixture of (R,S)-enantiomers of the epoxide of formula (I) to a microorganism or a preparation of said microorganism selected from the group consisting of *Trichosporon cutaneum*, *Geotrichum fragrans*, *Bacillus sphaericus*, *Pseudomonas aeruginosa*, *Serratia marcescens*, *Aspergillus oryzae* var. *magnasporus*, *Aspergillus sojae*, *Glycomyces rutgersensis*, *Saccharothrix australiensis*, *Streptomyces albosporeus* and *Pellicularia filamentosa*, (b) allowing the microorganism or preparation of said microorganism to preferentially open the epoxy ring of the (S)-entantiomer of formula (I) or to preferentially convert the (S)-enantiomer of formula (I) into the (R)-enantiomer of formula (I), and (c) recovering the (R)-enantiomer of formula (I), where R an alkyl group, an alkenyl group, a cycloalkyl group, an aryl group, an aralkyl group or a heterocyclic group, said groups optionally having a substituent selected from the group consisting of (1) a halogen atom, (2) a hydroxyl group, (3) a mercapto group, (4)

an amino group, (5) a nitro group, (6) an alkoxy group, (7) an alkenyloxy group, (8) a phenoxy group which may be substituted with (i) an alkyl group having 1–4 carbon atoms, (ii) an a alkoxy group having 1–4 carbon atoms or (iii) a halogen atom, (9) a naphthyloxy group which may be substituted with (i) an alkyl group having 1–4 carbon atoms, (ii) an alkoxy group having 1–4 carbon atoms or (iii) a halogen atom, (10) an aralkyloxy group, (11) an alkyl-thio group, (12) a carboxyl group, (13) a carbamoyl group, (14) a cyano group, and (15) an acyl group, wherein said cycloalkyl group, aryl group, aralkyl group and heterocyclic group represented by R may also be substituted with (16) an alkyl group, (17) an alkenyl group or (18) a haloalkyl group.

3. The process according to claim 1 or 2, wherein the enantiomeric mixture is a racemic mixture.

4. The process according to claim 1 or 2, further comprising growing said microorganism in a fluid medium, separating the microorganism from the medium, resuspending the cells in a buffer or water prior to adding the mixture of (R,S) epoxide of formula (I) as a solid, solution, suspension or dispersion.

5. The process according to claim 1 or 2, further comprising allowing the microorganism to preferentially open or convert the enantiomer of formula (I) at pH 3 to 9 and at a temperature of 10° to 60° C.

6. The process according to claim 1 or 2, further comprising adding the enantiomeric mixture in a concentration of 0.1 to 20% by weight.

7. The process according to claim 1 or 2, wherein R is phenyl group which may optionally be substituted with a halogen atom.

8. The process according to claim 1 or 2, wherein said heterocyclic group is selected from the group consisting of 3-furyl, furfuryl, 3-thienyl, 3-pyrrolyl, 3-pyrolidinyl, 2-pyridyl, 3-pyridyl, 4-pyridyl, 3-piperidinyl, 4-piperidinyl, 2-morpholinyl, 2-quinolyl, 3-quinolyl, 6-quinolyl, 4-isoquinolyl, 4-oxazoyl, 4-isooxazolyl, 4-thiazolyl, 1-imidazolyl, 4-imidazolyl, 4-pyrazolyl, 2-pyrazinyl, 5-pyrimidinyl, 4-pyridazinyl, 5-quinazolinyl, 3-benzofuranyl, 1-(2-pyrroylidonyl), and 9-carbazolyl.

9. The process according to claim 1 or 2, wherein R is an alkyl group having 1 to 10 carbon atoms; an alkenyl group having 2 to 6 carbon atoms; a cycloalkyl group having 3 to 8 carbon atoms; a phenyl group; a naphthyl group; an aralkyl group having 7 to 12 carbon atoms; a 5- to 7-membered heterocyclic group containing a nitrogen atom, an oxygen atom or a sulfur atom; an alkyl group having 1 to 10 carbon atoms or an alkenyl group having 2 to 6 carbon atoms, each group of which is substituted with at least one substituent selected from the group consisting of a hydroxyl group, an alkoxy group having 1 to 8 carbon atoms, an alkenyloxy group having 2 to 8 carbon atoms, an aryloxy group which may have an alkyl group having 1 to 4 carbon atoms, an alkoxy group having 1 to 4 carbon atoms or a halogen atom, and an aralkyloxy group having 7 to 18 carbon atoms; a cycloalkyl group having 3 to 8 carbon atoms, a phenyl group, a naphthyl group, an aralkyl group having 7 to 12 carbon atoms or a 5- to 7-membered heterocyclic group containing a nitrogen atom, an oxygen atom or a sulfur atom, each group of which is substituted with a least one substituent selected from the group consisting of a halogen atom, an alkoxy group having 1 to 5 carbon atoms, an alkyl group having 1 to 5 carbon atoms, a haloalkyl group having 1 to 5 carbon atoms and a nitro group.

10. The process according to claim 1 or 2, wherein R is an alkyl group having 1 to 6 carbon atoms; an alkenyl group having 2 to 4 carbon atoms; a phenyl group or an aralkyl group having 7 to 12 carbon atoms; an alkyl group having 1 to 6 carbon atoms or an alkenyl group having 2 to 4 carbon atoms, each group of which is substituted with at least one substituent selected from the group consisting of a hydroxy group and an alkenyl group having 2 to 8 carbon atoms; or a phenyl group or an aralkyl group having 7 to 12 carbon atoms, each group of which is substituted with at least one substituent selected from a halogen atom, an alkoxy group having 1 to 5 carbon atoms, an alkyl group having 1 to 5 carbon atoms, a haloalkyl group having 1 to 5 carbon atoms, and a nitro group.

* * * * *